United States Patent
Sturrock et al.

(10) Patent No.: US 11,129,805 B2
(45) Date of Patent: Sep. 28, 2021

(54) DUAL ACE C-DOMAIN/NEP INHIBITORS

(71) Applicant: ANGIODESIGN (UK) LIMITED, Warminster (GB)

(72) Inventors: Edward D. Sturrock, Warminster (GB); Mario R. W. Ehlers, Warminster (GB)

(73) Assignee: ANGIODESIGN (UK) LIMITED, Wiltshire (GB)

( * ) Notice: Subject to any disclaimer, the term of this patent is extended or adjusted under 35 U.S.C. 154(b) by 0 days.

(21) Appl. No.: 16/090,311

(22) PCT Filed: Mar. 31, 2017

(86) PCT No.: PCT/IB2017/051856
§ 371 (c)(1),
(2) Date: Oct. 1, 2018

(87) PCT Pub. No.: WO2017/168383
PCT Pub. Date: Oct. 5, 2017

(65) Prior Publication Data
US 2019/0111014 A1   Apr. 18, 2019

(30) Foreign Application Priority Data
Apr. 1, 2016 (GB) .................... 1605602

(51) Int. Cl.
*A61K 38/05* (2006.01)
*A61K 38/06* (2006.01)
*A61K 31/198* (2006.01)
*A61K 31/4035* (2006.01)
*A61P 9/12* (2006.01)

(52) U.S. Cl.
CPC ........ *A61K 31/198* (2013.01); *A61K 31/4035* (2013.01); *A61K 38/05* (2013.01); *A61K 38/06* (2013.01); *A61P 9/12* (2018.01)

(58) Field of Classification Search
None
See application file for complete search history.

(56) References Cited

U.S. PATENT DOCUMENTS

2003/0096761 A1* 5/2003 Burnside ................ A61K 9/485
514/211.05

OTHER PUBLICATIONS

Corti et al., "Vasopeptidase Inhibitors—A New Therapeutic Concept in Cardiovascular Disease?", Circulation, 2001, 1856-1862 (Year: 2001).*

Dimitropoulos et al. "A Computational Approach to the Study of the Binding Mode of Dual ACE/NEP Inhibitors", J. Chem. Inf. Model, 2010, 388-396 (Year: 2010).*

Klaire Labs, "Technical Notes: Magnesium Sterate", 2018; pp. 1-3 (Year: 2018).*

Sturrock et al.,"Structural basis for the C-domain-selective angiotensin-converting enzyme inhibition by brandykinin-potentiating peptide b (BPPb)", Biochemical Journal, May 2019, 1553-1570 (Year: 2019).*

Spyroulias "Peptidesubstrate selectivity and dual inhibitors of ACE and NEP vasopeptidases", Essays on Contemporary Peptide Science, 2011, 28 pages (Year: 2011).*

Cozier et al., "Crystal structures of sampatrilat and sampatrilat-Asp in complex with human ACE—a molecular basis for domain selectivity", The FEBS Journal, 2018, 1477-1490 (Year: 2018).*

Norton et al., "Sustained Antihypertensive Actions of a Dual Angiotensin-Converting Enzyme Neutral Endopeptidase Inhibitor, Sampatrilat, in Black Hypertensive Subjects", AJH 1999,563-571 (Year: 1999).*

Sharma et al., "Molecular Basis for Omapatrilat and Sampatrilat Binding to Neprilysin-Implications for Dual Inhibitor Design with Angiotensin-Converting Enzyme", J. Med. Chem., 2020, 5488-5500 (Year: 2020).*

Sharma et al., "Molecular Basis for Omapatrilat and Sampatrilat Binding to Neprilysin-Implications for Dual Inhibitor Design with Angiotensin-Converting Enzyme", Journal of Medicinal Chemistry, 2020, pp. 5488-5500 (Year: 2020).*

International Search Report and Written Opinion of the European Patent Office International Searching Authority. Application No. PCT/IB2017/051856, dated Jun. 14, 2017. 12 pages.

Burger, Dylan, et al. "Effects of a domain-selective ACE inhibitor in a mouse model of chronic angiotensin II-dependent hypertension." Clinical Science 127.1 (2014): 57-63.

Dimitropoulos, Nikolaos, et al. "A computational approach to the study of the binding mode of dual ACE/NEP inhibitors." Journal of chemical information and modeling 50.3 (2010): 388-396.

Dimitropoulos, Nikolaos, et al. "A computational approach to the study of the binding mode of dual ACE/NEP inhibitors Supporting Information." Journal of chemical information and modeling. Supporting Information. 50.3 (2010) 15 pages.

Jullien, Nicolas, et al. "Phosphinic tripeptides as dual angiotensin-converting enzyme C-domain and endothelin-converting enzyme-1 inhibitors." Journal of medicinal chemistry 53.1 (2010): 208-220.

Spyroulias, Georgios A. "Peptide substrate selectivity and dual inhibitors of ACE and NEP vasopetidases." In "Essays on Contemporary Peptide Science." Jan. 1, 2011, Research Signpost, XP055372614. 28 pages.

* cited by examiner

*Primary Examiner* — Lianko G Garyu
(74) *Attorney, Agent, or Firm* — Meunier Carlin & Curfman LLC

(57) ABSTRACT

A superior dual ACE/NEP inhibitor is a combination that selectively targets the ACE C-domain in addition to inhibiting NEP. Such a dual ACE C-domain/NEP inhibitor can be used in the treatment of diverse cardiovascular diseases, including hypertension and heart failure.

17 Claims, 4 Drawing Sheets

DUAL ACE C-DOMAIN/NEP INHIBITORS

BACKGROUND OF THE INVENTION

THIS invention relates to dual ACE C-domain/NEP inhibitors that simultaneously and selectively inhibit the angiotensin-converting enzyme (ACE) C-domain and neutral endopeptidase (NEP), and their use in the treatment of diverse cardiovascular diseases.

Over the past 20 years, the importance of ACE and the renin-angiotensin system (RAS) in cardiovascular physiology and disease have become firmly established, mainly as a result of the use of drugs that block various components of this system, including ACE inhibitors, angiotensin II receptor blockers, and aldosterone antagonists. These drugs are now first-line treatments for hypertension (high blood pressure), heart failure, prevention of vascular events (mainly heart attack and stroke), and slowing kidney disease due to hypertension or diabetes. The involvement of ACE and the RAS in so many different cardiovascular diseases is explained by the fact that the peptide hormone angiotensin II has numerous biological effects [M. Ruiz-Ortega et al. (2001) Role of the renin-angiotensin system in vascular diseases: expanding the field. *Hypertension* 38: 1382-1387].

Angiotensin II is produced by the action of ACE on a precursor called angiotensin I. Angiotensin II is a powerful vasoconstrictor, which means it causes blood vessels to narrow, raising blood pressure. Angiotensin II also stimulates the release of the hormone aldosterone from the adrenal glands, which in turn signals the kidneys to retain salt and water, which further raises blood pressure. Furthermore, angiotensin II acts as a growth factor that stimulates thickening of the blood vessel walls, aggravating the process of atherosclerosis, or hardening of the arteries. Therefore, drugs acting on ACE and the RAS reduce blood pressure, improve the function of the heart, and slow down the progression of atherosclerosis and kidney disease. However, angiotensin II is not the only peptide metabolized by ACE.

ACE also acts on other peptide hormones, notably bradykinin, which has the opposite effect of angiotensin II; that is, it is a vasodilator. When ACE is inhibited, this results not only in reduced levels of angiotensin II (therefore, less vasoconstriction) but also in increased levels of bradykinin (therefore, more vasodilatation), which means there is an even greater lowering of blood pressure than if the effect was on angiotensin II alone. Moreover, bradykinin also has anti-inflammatory effects, all of which explains why ACE inhibitors have a different therapeutic profile than drugs that only block the angiotensin II receptor.

Work on the current-generation ACE inhibitors first began in 1967 at the Squibb Institute for Medical Research and ended 10 years later in the synthesis of captopril, the first orally active, therapeutically useful ACE inhibitor, which is still in use today. The development of captopril was made possible by two discoveries: (1) venom peptides from the Brazilian pit viper inhibit ACE, and (2) ACE is a zinc-dependent enzyme similar to carboxypeptidase-A (CPDA), one of the few enzymes for which an x-ray structure was available at the time. Therefore, although there was no structural information on ACE itself, the information from the venom peptides and CPDA enabled a limited rational design approach that was ultimately successful [M. A. Ondetti et al. (1977) Design of specific inhibitors of angiotensin-converting enzyme: new class of orally active antihypertensive agents. *Science* 196: 441-444; Cushman & Ondetti (1999)].

Captopril is very effective, but it has the specific disadvantage of a bad taste and chemical instability, due the presence of a thiol group. Captopril was followed by the development of enalapril and lisinopril by Merck after it was shown that several different functional groups could substitute for the thiol in captopril to bind to the active-site zinc in ACE, a critical feature required for the potency and specificity of ACE inhibitors [B. Holmquist & B. L. Vallee (1979) Metal-coordinating substrate analogs as inhibitors of metalloenzymes. *Proc. Natl. Acad. Sci. USA* 76: 6216-6220; A. A. Patchett et al. (1980) A new class of angiotensin-converting enzyme inhibitors. *Nature* 288: 280-283]. The work by Holmquist & Vallee not only foreshadowed the Merck compounds, which use a carboxylate for binding to the zinc, but paved the way for subsequent inhibitors using phosphinic acid and hydroxamate zinc-binding groups. Ultimately, more than ten ACE inhibitors were developed, but all were based on the original concepts that guided the design of captopril.

All current-generation ACE inhibitors are similar in their efficacy and side effect profiles, with minor differences in potency and pharmacokinetic properties. The principal side effects include cough and various skin reactions, of which the most serious is life-threatening angioedema; the overall incidence of side effects is estimated at 28% [Steckelings et al. (2001); M. A. Weber & F. H. Messerli (2008) Angiotensin-converting enzyme inhibitors and angioedema. Estimating the risk. *Hypertension* 51: 1465-1467]. More recently, ACE inhibitors have also been shown to cause mild to moderate anemia. These side effects are likely due to effects of ACE inhibitors on peptides other than angiotensin II, including peptides such as bradykinin, luteinizing hormone-releasing hormone (LHRH), N-Ac-SDKP, and substance P, some of which are preferentially or exclusively hydrolyzed by the N domain of ACE.

A second major peptide hormone system that influences blood pressure, fluid and electrolyte homeostasis, renal function, and cardiovascular function is the natriuretic peptide system. Natriuretic peptides (NPs) comprise atrial, brain, and C-type natriuretic peptides (ANP, BNP, and CNP, respectively), which principally mediate natriuretic, diuretic, vasorelaxant, and antimitogenic responses largely directed to reduce blood pressure and maintain fluid volume homeostasis [reviewed by K. N. Pandey (2005) Biology of natriuretic peptides and their receptors. *Peptides* 26: 901-932]. The existence of three NPs revealed that their role in the control of atrial pressure and cardiovascular regulation is complex and this complexity is increased by the prevalence of three different NP-specific cell surface receptor proteins: NP receptor-A (NPRA), receptor-B (NPRB), and receptor-C (NPRC). Both NPRA and NPRB contain guanylyl cyclase (GC) catalytic activity and are also referred to as GC-A and GC-B, respectively; however, NPRC functions without GC activity. Importantly, there is cross-regulation between the RAS and NP systems [K. N. Pandey (2005) Biology of natriuretic peptides and their receptors. *Peptides* 26: 901-932], with important implications for the design of therapeutic modalities that augment or inhibit these peptide hormone systems in the treatment of cardiovascular and related diseases.

Circulating NPs are cleared through 2 principal mechanisms: NP receptor-mediated clearance and enzyme degradation [L. R. Potter (2011) Natriuretic peptide metabolism, clearance and degradation. FEBS J. 278: 1808-1817]. A neutral glycosylated zinc endopeptidase in the proximal tubule cells of the kidney is a potent hydrolyzer of ANP. The production and release of this enzyme—variously known as atriopeptidase, neutral endopeptidase, EC 3.4.24.11, enkephalinase, common acute lymphoblastic leukemia antigen, CD10, or neprilysin (NEP)—from endothelial cells contributes to its presence in the circulation. The abundance of this peptidase in the renal cortex contributes to the very brief half-life of ANP (approximately 2 min in normal human subjects). Although attention was initially directed to its ability to hydrolyze ANP, this membrane-bound enzyme with a large extracellular component also degrades a large number of other vasoactive peptides, including adrenomedullin (ADM), bradykinin, angiotensins I and II, and endothelin-1, as well as oxytocin, opioid peptides, substance P, gastrin, vasoactive intestinal peptide, and amyloid beta protein [C. Oefner et al. (2000) Structure of human neutral endopeptidase (neprilysin) complexed with phosphoramidon. J. Mol. Biol. 296: 341-349].

A number of NEP inhibitors have been described, including thiorphan, ecadotril, candoxatril, and sacubitril. The design and synthesis of these compounds was based on screening by enzyme inhibition and the presumed similarity of NEP to other, better-characterized Zn-metalloproteases such as thermolysin. More recently, after the crystal structure of NEP was determined, including in complex with thiorphan, efforts have been made to develop newer-generation NEP inhibitors by structure-based design [K. Misawa et al. (2011) Structure-based design of dipeptide derivatives for the human neutral endopeptidase. Bioorg. Med. Chem. 19: 5935-5947].

The effects of NEP inhibition are attributed in most part to the increased biological activity of natriuretic peptides that results from their reduced degradation. In heart failure patients, ANP infusion increases cardiac index by reducing systemic vascular resistance, and similar benefits result from BNP infusion [W. S. Colucci et al. (2000) Intravenous nesiritide, a natriuretic peptide, in the treatment of decompensated congestive heart failure. Nesiritide Study Group. N. Engl. J. Med. 343: 246-253]. NEP inhibition potentiates plasma levels and effects of administered natriuretic peptide but has variable effects on plasma levels of endogenous natriuretic peptide because any tendency of NEP inhibition to increase peptide levels by inhibiting metabolism may be negated by reduced natriuretic peptide secretion caused by a diuresis- and natriuresis-induced reduction in cardiac filling pressures [E. J. Sybertz et al. (1990) Atrial natriuretic factor-potentiating and antihypertensive activity of SCH 34826: an orally active neutral metalloendopeptidase inhibitor. Hypertension 15: 152-161].

NEP inhibition has quite variable effects on blood pressure. There may be no change, a decrease, or an increase in blood pressure of normotensive and hypertensive human subjects in response to NEP inhibition [B. Favrat et al. (1995) Neutral endopeptidase versus angiotensin converting enzyme inhibition in essential hypertension. J. Hypertens. 13: 797-804; D. J. Campbell (2003) Vasopeptidase inhibition. A double-edged sword? Hypertension 41: 383-389]. Moreover, NEP inhibition can lead to both increased or unchanged systemic vascular resistance in heart failure patients depending on the duration of therapy [M. Kentsch et al. (1996) Neutral endopeptidase 24.11 inhibition may not exhibit beneficial haemodynamic effects in patients with congestive heart failure. Eur. J. Clin. Pharmacol. 51: 269-272]. The variable effect of NEP inhibition on blood pressure and systemic vascular resistance is likely to be a response to the increased levels of the many different vasoactive peptides metabolized by NEP. In addition to increased levels of vasodilator peptides (NPs and BK), NEP inhibition may increase levels of the vasoconstrictors Ang II and endothelin, and reduce levels of the vasodilator Ang-(1-7). In turn, in addition to increasing endothelin levels, both animal and clinical studies show that NEP inhibition impairs the metabolic clearance of Ang II and increases plasma levels of Ang I, Ang II, aldosterone, and catecholamines [D. J. Campbell (2003) Vasopeptidase inhibition. A double-edged sword? Hypertension 41: 383-389].

It was hoped that NEP inhibitors would become useful in the management of hypertension and heart failure, but these beneficial effects in patients were modest and were not seen in all studies [J. G. Cleland & K. Swedberg for the International Ecadotril Multi-centre Dose-ranging Study Investigators. (1998) Lack of efficacy of neutral endopeptidase inhibitor ecadotril in heart failure. Lancet 351: 1657-8]. In addition to increasing the concentration of circulating ANP, NEP inhibitors were found to increase the concentration of 2 other circulating vasodilators, adrenomedullin and bradykinin [M. A. Weber (2001) Vasopeptidase inhibitors. Lancet 358: 1525-1532]. However, they also increased the concentration of 2 circulating pressors, angiotensin II and endothelin I [C. J. Ferro et al. (1998) Inhibition of neutral endopeptidase causes vasoconstriction of human resistance vessels in vivo. Circulation 97: 2323-2330]. These 2 opposing actions, that is, inhibition of degradation of both vasoconstrictor and vasodilator peptides, neutralized each other and, as a consequence, NEP inhibitors alone had little effect on blood pressure [S. Ando et al. (1995) Comparison of candoxatril and atrial natriuretic factor in healthy men. Effects on hemodynamics, sympathetic activity, heart rate variability, and endothelin. Hypertension 26: 1160-1166] or heart failure [J. G. Cleland & K. Swedberg for the International Ecadotril Multi-centre Dose-ranging Study Investigators. (1998) Lack of efficacy of neutral endopeptidase inhibitor ecadotril in heart failure. Lancet 351: 1657-8].

With the discovery and elucidation of the actions of NEP and its inhibitors, both the similarities and differences between the RAS and the NP system became clearer. In normal subjects, the RAS is activated, in part, by reduced stretch of the efferent renal arterioles as well as by stimulation of beta-1-adrenergic receptors through activation of the sympathetic nervous system. Activation of the sympathetic nervous system and RAS provides an adaptive response to hypovolemia, hypotension, and sodium deprivation. This response includes the release of renin, mostly from granular juxtaglomerular cells in the walls of the afferent arterioles of the kidney, leading to the production of the pressor angiotensin II. This, in turn, causes vasoconstriction of renal efferent arterioles, as well as release of aldosterone, increasing sodium reabsorption in the collecting duct. However, because these actions are maladaptive when they occur in patients with HF or hypertension, reducing the generation of angiotensin II by ACE inhibitors are beneficial in these conditions. In contrast, atrial and/or ventricular distension, as occurs in heart failure and hypertension, causes the release of NPs from the heart, which results in vasodilation and natriuresis. Although these actions are beneficial (adaptive) in patients with HF or hypertension, rapid enzymatic degradation of ANP by endogenous NEP greatly diminishes their vasorelaxant, natriuretic, and diuretic actions. NEP inhibitors, while raising the concentration of circulating vasodilator peptides, especially ANP, have complex actions (as outlined earlier) and appear by themselves not to be useful in the treatment of either HF or hypertension.

Since the previously mentioned elevation of circulating angiotensin II by NEP inhibitors neutralizes its salutary vasorelaxant and natriuretic actions, it appeared logical to ascertain whether the suppression of angiotensin II production would correct this problem. In an important study published in 1991, treatment of hypertensive rats by separate administrations of a selective NEP inhibitor and of the ACE inhibitor captopril were compared, as well as their simultaneous administration. As predicted, the combination resulted in a greater reduction of arterial pressure than each inhibitor given separately [A. A. Seymour et al. (1991) Antihypertensive activity during inhibition of neutral endopeptidase and angiotensin converting enzyme. *J. Cardiovasc. Pharmacol.* 17: 456-65]. A similar result was achieved in human hypertension when patients were administered either an NEP inhibitor or ACE inhibitor alone or the combination [B. Favrat et al. (1995) Neutral endopeptidase versus angiotensin converting enzyme inhibition in essential hypertension. *J. Hypertens.* 13: 797-804]. These observations on the greater efficacy of dual therapy were confirmed in cardiomyopathic hamsters [N. C. Trippodo N C et al. (1999) Vasopeptidase inhibition with omapatrilat improves cardiac geometry and survival in cardiomyopathic hamsters more than does ACE inhibition with captopril. *J. Cardiovasc. Pharmacol.* 34: 782-90], as well as in sheep with pacing-induced heart failure [M. T. Rademaker et al. (1998) Combined neutral endopeptidase and angiotensin-converting enzyme inhibition in heart failure: role of natriuretic peptides and angiotensin II. *J. Cardiovasc. Pharm.* 31: 116-25]. The next important step was to develop orally active molecules that inhibited both ACE and NEP, that is, dual inhibitors, which was first accomplished in 1994 [M.-C. Fournie-Zaluski et al. (1994) New dual inhibitors of neutral endopeptidase and angiotensin-converting enzyme: rational design, bioavailability, and pharmacological responses in experimental hypertension. *J. Med. Chem.* 37: 1070-1083].

Due to the potential promise of oral dual inhibitors, referred to as vasopeptidase inhibitors, several pharmaceutical companies entered the field. Omapatrilat was the drug in this class that underwent the most extensive clinical testing [J. A. Robl et al. (1997) Dual metalloprotease inhibitors: mercaptoacetyl-based fused heterocyclic dipeptide mimetics as inhibitors of angiotensin-converting enzyme and neutral endopeptidase. *J. Med. Chem.* 40: 1570-1577]. It produced greater reductions in arterial pressure than did the ACE inhibitor, lisinopril, in patients with hypertension and increased the excretion of ANP, confirming that the dose used also exerted significant inhibition of NEP [V. M. Campese et al. (2001) Omapatrilat versus lisinopril: efficacy and neurohormonal profile in salt-sensitive hypertensive patients. *Hypertension* 38: 1342-8]. IMPRESS (Inhibition of Metalloprotease by Omapatrilat in a Randomized Exercise and Symptoms Study in Heart Failure), a randomized clinical trial, compared omapatrilat with lisinopril in 573 patients with heart failure; a trend toward greater benefit with omapatrilat was reported [J. L. Rouleau et al. (2000) Comparison of vasopeptidase inhibitor, omapatrilat, and lisinopril on exercise tolerance and morbidity in patients with heart failure. IMPRESS randomised trial. *Lancet* 356: 615-20].

However, in a phase 3 trial in heart failure, the OVERTURE (Omapatrilat Versus Enalapril Randomized Trial of Utility in Reducing Events) trial, comparison of omapatrilat with enalapril in 5,770 patients with heart failure failed to show superiority of omapatrilat in the primary endpoint (all-cause mortality or hospitalization for heart failure) [M. Packer et al. (2002) Comparison of omapatrilat and enalapril in patients with chronic heart failure. The Omapatrilat versus Enalapril Randomized Trial of Utility in Reducing Events (OVERTURE). *Circulation* 106: 920-926]. Moreover, angioedema, which can obstruct the upper airways, occurred more frequently with omapatrilat (0.8%) than with enalapril (0.5%). In order to obtain a clearer understanding of the frequency of this complication, and, in particular, to compare omapatrilat with an ACE inhibitor, enalapril, the OCTAVE (Omapatrilat Cardiovascular Treatment vs. Enalapril) trial was conducted in 25,302 hypertensive subjects. As expected, omapatrilat was superior to enalapril in reducing blood pressure. However, the incidence of angioedema was again significantly higher and more severe in the subjects treated with omapatrilat (2.17%) than in those receiving lisinopril (0.68%). Among African American patients, the incidence was greater for both agents (5.53% vs. 1.62%) [J. B. Kostis et al. (2004) Omapatrilat and enalapril in patients with hypertension: the Omapatrilat Cardiovascular Treatment vs. Enalapril (OCTAVE) trial. *Am. J. Hypertens.* 17: 103-111]. The increased incidence of this serious, potentially life-threatening complication was presumed to be related to the synergism between the ACE- and NEP-inhibiting actions of omapatrilat on the degradation of bradykinin. Omapatrilat inhibits a third enzyme, aminopeptidase P, which is also involved in the breakdown of bradykinin [R. M. Fryer et al. (2008) Effect of bradykinin metabolism inhibitors on evoked hypotension in rats: rank efficacy of enzymes associated with bradykinin-mediated angioedema. *Br. J. Pharmacol.* 153: 947-955]. Bradykinin is not only a vasodilator, but it also enhances prostaglandin concentrations and increases vascular permeability and fluid extravasation. Hence, the question was raised as to whether omapatrilat, which initially appeared to be an attractive drug, could be a "double-edged sword" [D. J. Campbell (2003) Vasopeptidase Inhibition. A double-edged sword? *Hypertension* 41: 383-389]. Primarily on the basis of observations of increased angioedema in the OCTAVE trial, efforts to gain approval of omapatrilat and, indeed, further clinical research on the entire class of vasopeptidase inhibitors were halted.

The aforementioned examples illustrate that, despite decades of research in structure-function relationships in peptidases that metabolize vasoactive peptides, in preclinical models of cardiovascular diseases, and in clinical research, significant uncertainties remain in regard to the physiology and pathophysiology of vasoactive peptide systems and their effect on cardiovascular function and diseases. In particular, uncertainties remain about the effects of modulating (inhibiting or augmenting) the function of various peptidases that metabolize said vasoactive peptides, specifically the peptidases ACE and NEP, and how such modulation will translate into changes in vasoactive peptide networks and their downstream effects. The range of peptides metabolized by ACE and NEP is so diverse and extensive, often with opposing actions, that it is difficult or impossible to predict the results of peptidase inhibition and the consequent changes in peptide networks [D. J. Campbell (2016) Long-term neprilysin inhibition—implications for ARNIs. *Nat. Rev. Cardiol.* Advanced online publication 15 Dec 2016; J. L. Januzzi & N. E. Ibrahim (2017) Renin-angiotensin system blockade in heart failure. More to the picture than meets the eye. *J. Am. Coll. Cardiol.* 69: 820-822].

These uncertainties have highlighted that new technologies are required better to understand the effects of peptidase modulation on the composition of vasoactive peptide networks and their potential downstream effects. Such advances will in turn enable new insights that heretofore could not be predicted based on current knowledge. An example of such new technology is the use of advanced liquid chromatography/mass spectrometry to "fingerprint" angiotensin and related vasoactive peptides and to evaluate the impact of peptidase modulation on the production and relative ratios of these various peptides. Deployment of this new technology has revealed that changes in peptide ratios are different from and more complex than previously assumed. Importantly, these new insights correlate with clinical outcomes and prognosis in acute and chronic heart failure in response to therapeutic interventions and indicate that angiotensin metabolic profiling may enable a better assessment of heart failure status and selection of therapies for heart failure [R. Basu et al. (2017) Roles of angiotensin peptides and recombinant human ACE2 in heart failure. *J. Am. Coll. Cardiol.* 69: 805-819]. Thus, use of RAS fingerprinting provides correlations with clinical outcomes that are as good as, or superior to, results obtained in relevant animal models.

SUMMARY OF THE INVENTION

According to a first aspect of the invention, there is provided a selective dual ACE/NEP inhibitor, the dual ACE/NEP inhibitor being selective for the C-domain active site of ACE and for the NEP active site.

According to a second aspect of the invention, there is provided a method of treating a cardiovascular disease, where such cardiovascular disease is selected from:
 a. hypertension (high blood pressure);
 b. heart failure, including congestive heart failure, heart failure with reduced left ventricular (LV) ejection fraction (HFrEF), heart failure with preserved LV ejection fraction (HFpEF), left ventricular dysfunction, right-sided heart failure, right ventricular dysfunction, and general states of reduced cardiac output;
 c. atherosclerosis and atherosclerotic vascular disease, including coronary heart disease and coronary artery disease;
 d. myocardial infarction (heart attack), including acute coronary syndrome;
 e. nephropathy (kidney dysfunction) associated with hypertension or diabetes;
 f. stroke, including infarction of the brain or any part of the brain due to cerebral artery occlusion, thrombosis, or haemorrhage, comprising administering to a patient in need of such treatment a therapeutically effective amount of a selective dual ACE/NEP inhibitor, the dual ACE/NEP inhibitor being selective for the C-domain active site of ACE and for the NEP active site.

According to a third aspect of the invention, there is provided a selective dual ACE/NEP inhibitor, the dual ACE/NEP inhibitor being selective for the C-domain active site of ACE and for the NEP active site, for use in a method of treatment of a cardiovascular disease, in such cardiovascular disease is selected from:
 a. hypertension (high blood pressure);
 b. heart failure, including congestive heart failure, heart failure with reduced left ventricular (LV) ejection fraction (HFrEF), heart failure with preserved LV ejection fraction (HFpEF), left ventricular dysfunction, right-sided heart failure, right ventricular dysfunction, and general states of reduced cardiac output;
 c. atherosclerosis and atherosclerotic vascular disease, including coronary heart disease and coronary artery disease;
 d. myocardial infarction (heart attack), including acute coronary syndrome;
 e. nephropathy (kidney dysfunction) associated with hypertension or diabetes;
 f. stroke, including infarction of the brain or any part of the brain clue to cerebral artery occlusion, thrombosis, or haemorrhage.

According a fourth aspect of the invention, there is provided a composition comprising a selective dual ACE/NEP inhibitor, the dual ACE/NEP inhibitor being selective for the C-domain active site of ACE and for the NEP active site as hereinbefore defined.

In a preferred embodiment of this aspect of the invention, the composition is a pharmaceutical composition further comprising a pharmaceutically acceptable carrier, together with other optional pharmaceutically acceptable excipients.

In some preferred embodiments of the invention, the dual ACE C-domain/NEP inhibitor is administered by the oral route in the form of a tablet, capsule, or other pharmaceutical formulation suitable for oral administration. Oral administration can be once per day, twice per day, three times per day, or four times per day.

In some preferred embodiments of the invention, the dual ACE C-domain/NEP inhibitor is administered by the parenteral route, such as intravenously, intramuscularly, or subcutaneously, in a pharmaceutical formulation suitable for parenteral administration. Parenteral administration can be once per day, twice per day, three times per day, or four times per day.

According to another aspect of the invention, there is provided a combination of an inhibitor selective for the C-domain active site of ACE and an inhibitor of the NEP active site, the selective C-domain inhibitor and NEP inhibitor being selected such as selectively to inhibit the conversion of angiotensin I to angiotensin II and the breakdown of natriuretic peptides whilst preserving bradykinin metabolism.

According to yet a further aspect of the invention, there is provided a combination of an inhibitor selective for the C-domain active site of ACE and an inhibitor of the NEP active site for use in the treatment of a cardiovascular disease, where such cardiovascular disease is selected from:
 a. hypertension (high blood pressure);
 b. heart failure, including congestive heart failure, heart failure with reduced left ventricular (LV) ejection fraction (HFrEF), heart failure with preserved LV ejection fraction (HFpEF), left ventricular dysfunction, right-sided heart failure, right ventricular dysfunction, and general states of reduced cardiac output;
 c. atherosclerosis and atherosclerotic vascular disease, including coronary heart disease and coronary artery disease;
 d. myocardial infarction (heart attack), including acute coronary syndrome;
 e. nephropathy (kidney dysfunction) associated with hypertension or diabetes;
 f. stroke, including infarction of the brain or any part of the brain due to cerebral artery occlusion, thrombosis, or hemorrhage.

In some embodiments of the invention the combination is administered by the oral route in a form that combines both compounds (the ACE C-domain inhibitor and the NEP inhibitor) in a single formulation, where such formulation can be a tablet, capsule, or other pharmaceutical formulation suitable for oral administration. Oral administration can be once per day, twice per day, three times per day, or four times per day.

In some embodiments of the invention the combination is administered by the parenteral route, such as intravenously, intramuscularly, or subcutaneously, in a pharmaceutical formulation that combines both compounds (the ACE C-domain inhibitor and the NEP inhibitor) in a single formulation suitable for parenteral administration. Parenteral administration can be once per day, twice per day, three times per day, or four times per day.

BRIEF DESCRIPTION OF THE DRAWINGS

Without thereby limiting the scope, the invention will now be described in more detail with reference to the accompanying Figures in which.

DESCRIPTION OF PREFERRED EMBODIMENTS

Figure 1A:
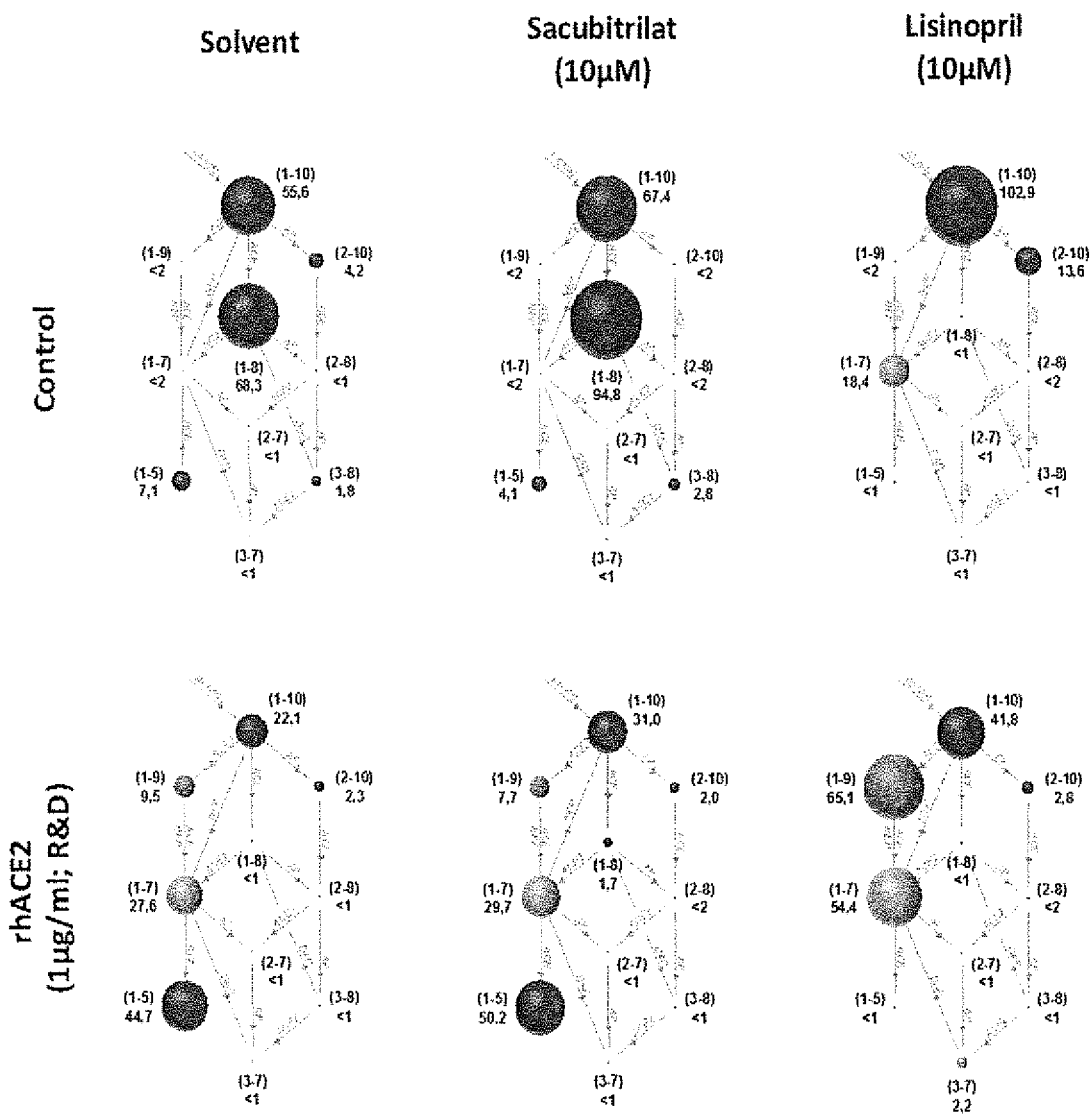
FIG. 1A represents the RAS equilibrium analysis in human plasma in the presence of 1% water (solvent), and the drugs sacubitrilat and lisinopril. Recombinant human neutral endopeptidase (rhNEP) was added to all samples at a concentration of 200 pg/ml. In the bottom panel recombinant human angiotensin-converting enzyme 2 (rhACE2) was added at a concentration of 1 µg/ml. The sizes of spheres reflect the concentration of the corresponding angiotensin metabolite, which sequence is given in brackets next to the sphere (1-10=Ang I, DRVYIHPFHL). Concentrations are given in pg/ml below the metabolite sequence.
Figure 1B:
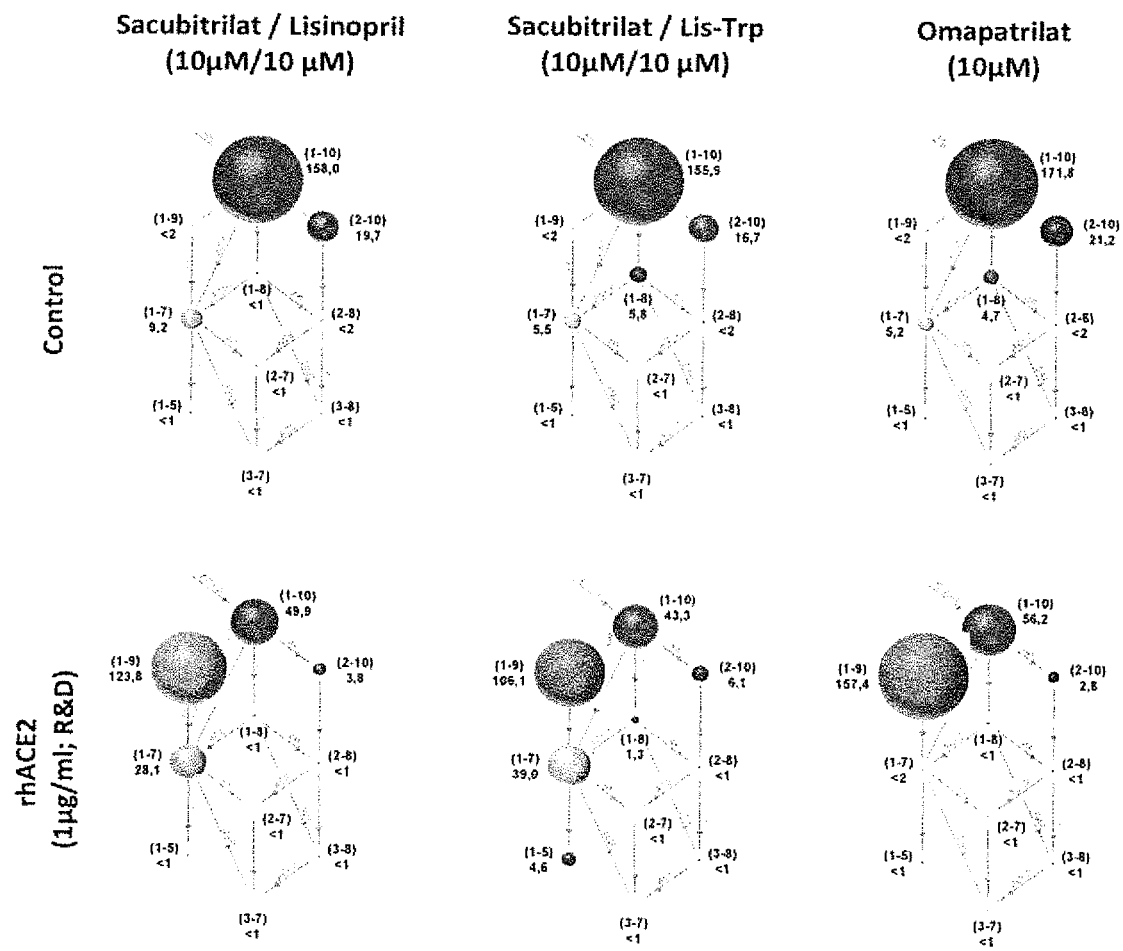
FIG. 1B represents the RAS equilibrium analysis in human plasma in the presence of sacubitrilat and lisinopril, sacubitrilat and Lis-Trp, and omapatrilat, Recombinant human neutral endopeptidase (rhNEP) was added to all samples at a concentration of 200 pg/ml. In the bottom panel recombinant human angiotensin-converting enzyme 2 (rhACE2) was added at a concentration of 1 µg/ml. The sizes of spheres reflect the concentration of the corresponding angiotensin metabolites, which sequence is given in brackets next to the sphere (1-10=Ang I, DRVYIHPFHL). Concentrations are given in pg/ml below the metabolite sequence.

A superior dual ACE/NEP inhibitor of the invention is a combination that selectively targets the ACE C-domain in addition to inhibiting NEP, i.e., a dual ACE C-domain-selective/NEP inhibitor, which henceforth is called a C-dom/NEP inhibitor for convenience.

The terms "angiotensin-converting enzyme" and "ACE" as used in the context of the present invention can be comprised of full-length wild-type ACE, either the somatic or the testis isoforms, or of various fragments of ACE proteins, notably the isolated N and C domains of the enzyme or derivatives thereof, or of said angiotensin-converting enzyme proteins that contain one or more site-specific or regional mutations, deletions, truncations, insertions, glycosylation changes, or other modifications that facilitate or enhance protein expression, purification, crystallization, x-ray diffraction, or x-ray structure determination or refinement. It is important to note that angiotensin-converting enzyme or ACE is also referred to in the literature as "angiotensin I-converting enzyme," "converting enzyme," "dipeptidyl carboxypeptidase," "petidyldipeptide hydrolase," or "kininase II"; these terms are all synonymous with angiotensin-converting enzyme and ACE, and this enzyme is classified by the International Union of Biochemists as EC 3.4.15.1 [M. R. W. Ehlers & J. F. Riordan (1990) Angiotensin-converting enzyme. Biochemistry and molecular biology. In *Hypertension: Pathophysiology, Diagnosis, and Management* (J. H. Laragh & B. M. Brenner, eds.), pp. 1217-1231, Raven Press, New York]. Two forms or isoforms of ACE are known: somatic ACE (also referred to as endothelial or lung ACE) and testis ACE (also referred to as testicular or germinal ACE). Cloning of the ACE gene cDNA revealed that there is a single ACE gene that generates two distinct mRNAs, the somatic ACE mRNA and the testis ACE mRNA, by the use of tissue-specific promoter sites. Further, it was found that the somatic form of ACE consists of two homologous domains arranged in tandem in a single polypeptide chain, termed the N and C domains (referring to their N- and C-terminal locations, respectively, in the polypeptide), and each domain contains an active site characterized by the classic HEXXH zinc-binding motif of metallopeptidases and the presence of 1 zinc atom per active site.

Moreover, the testis form of ACE consists of only a single domain, which is identical to the C domain in somatic ACE [K. R. Acharya et al. (2003) ACE revisited: a new target for structure-based drug design. *Nat Rev. Drug Discov.* 2: 891-902].

The terms "neutral endopeptidase" and "NEP" as used in the context of the present invention can be comprised of full-length wild-type NEP, or of various fragments of NEP proteins, notably isolated domains of the enzyme or derivatives thereof, or of said neutral endopeptidase proteins that contain one or more site-specific or regional mutations, deletions, truncations, insertions, glycosylation changes, or other modifications that facilitate or enhance protein expression, purification, crystallization, x-ray diffraction, or x-ray structure determination or refinement. It is important to note that neutral endopeptidase or NEP is also referred to in the literature as "enkephalinase," "neprilysin," "membrane metallo-endopeptidase (MME)," "cluster of differentiation 10 (CD10)," and "common acute lymphoblastic leukemia antigen (CALLA)"; these terms are all synonymous with neutral endopeptidase and NEP, and this enzyme is classified by the International Union of Biochemists as EC 3.4.24.11.

By inhibiting only the C-domain active site of ACE, a C-dom/NEP inhibitor will produce favorable changes in levels of vasoactive peptides, i.e., decreased angiotensin II (Ang II) and increased natriuretic peptides levels, while at the same time leaving bradykinin (BK) levels in the normal range. Although NEP is a BK-metabolizing enzyme, the activity of ACE is dominant in this regard [R. M. Fryer et al. (2008) Effect of bradykinin metabolism inhibitors on evoked hypotension in rats: rank efficacy of enzymes associated with bradykinin-mediated angioedema. *Br. J. Pharmacol.* 153: 947-955].

Moreover, the metabolizing capacity of each active site in ACE is such that either site alone (i.e., either the N-domain or C-domain active site) can fully metabolize physiological levels of BK even when the second site is inhibited [D. Georgiadis et al. (2003) Roles of the two active sites of somatic angiotensin-converting enzyme in the cleavage of angiotensin I and bradykinin. Insights from selective inhibitors. *Circ Res.* 93: 148-154; D. Burger et al. (2014) Effects of a domain-selective ACE inhibitor in a mouse model of chronic angiotensin II-dependent hypertension. *Clin. Sci.* 127: 57-63]. In the case of a C-domlNEP inhibitor, the uninhibited N-domain active site will metabolize physiologic amounts of BK and ensure that excessive BK build-up will not occur. In this regard, a C-dom/NEP inhibitor is fundamentally different from the vasopeptidase inhibitors, such as omapatrilat.

Since a C-dom/NEP inhibitor does not produce elevated BK levels, treatment of hypertension or heart failure does not result in unfavorable excessive vasodilatation and both the safety and efficacy profiles are optimized. Specifically, compared to placebo, there is no increased risk of angioedema, cough, flushing, facial redness, or gastrointestinal symptoms; further, compared to a conventional ACE inhibitor, a C-dom/NEP inhibitor shows superior efficacy in the treatment of hypertension and heart failure.

A further improvement of the C-dom/NEP inhibitor of the invention compared to vasopeptidase inhibitors, including omapatrilat, is lack of inhibitory activity towards a third protease, aminopeptidase P (APP). It is now known that APP is a third protease (peptidase) involved in the metabolism of BK, and, in fact, it appears to be quantitatively more important in this regard than NEP [R. M. Fryer et al. (2008) Effect of bradykinin metabolism inhibitors on evoked hypotension in rats: rank efficacy of enzymes associated with bradykinin-mediated angioedema. *Br. J. Pharmacol.* 153: 947-955]. Inhibition of APP was an unintended pharmacologic property of omapatrilat. The design and synthesis of omapatrilat and related compounds was based on general compound screening and structure-activity relationship (SAR) methods and not on high-precision, structured-based drug-design methods because the high-resolution crystal structures of ACE and NEP were not available at the time [N. G. Delaney et al. (1994) Mercaptoacyl dipeptides as dual inhibitors of angiotensin-converting enzyme and neutral endopeptidase. Preliminary structure-activity studies. *Bioorg. Med. Chem. Lett.* 4: 1783-1788; J. A. Robl et al. (1997) Dual metalloprotease inhibitors: mercaptoacetyl-based fused heterocyclic dipeptide mimetics as inhibitors of angiotensin-converting enzyme and neutral endopeptidase. *J. Med. Chem.* 40: 1570-1577]. By contrast, the highly optimized C-dom/NEP inhibitors of the current invention eliminate inhibitory activity towards APP.

In addition to hypertension, the C-dom/NEP inhibitors of the invention can be used in the treatment of a variety of human disease states, including but not limited to: congestive heart failure; heart failure with reduced ejection fraction; heart failure with preserved ejection fraction; left ventricular dysfunction; atherosclerosis and complications of atherosclerotic disease; prevention of stroke, myocardial infarction and other vascular ischemic events; type 2 diabetes mellitus, insulin resistance, and the metabolic syndrome; and prevention and treatment of progressive renal impairment and end-stage renal disease.

It can be seen that there is a real and continuing need for C-dom/NEP inhibitors that are highly C-domain-selective, and that improve the therapeutic efficacy of vasopeptidase inhibition and improve the side effect profile.

A fundamental flaw of all current-generation ACE inhibitors—be they conventional ACE inhibitors or dual ACE/NEP inhibitors—is that they are mixed, non-selective inhibitors of both the N- and C-domain active sites of the ACE enzyme. Until the molecular cloning of the ACE gene, expression of the full-length protein, and, crucially, expression of the N- and C-domains in isolation, ACE was assumed to comprise a polypeptide with a single active site and this was the basis for all ACE inhibitor drug design and development, including vasopeptidase inhibitors. It is now known that ACE consists of two similar but non-identical domains (the N and C domains) and that each domain contains a unique active site with different enzyme activities. Extensive experimental work with both the full-length and isolated domains in vitro and in viva, including the use of transgenic mouse models and pharmacodynamics work with domain-selective inhibitors in relevant animal models, has shown that the two active sites play distinct physiological roles.

Both the N and the C domain of ACE convert angiotensin I to angiotensin II; however, in the full-length, 2-domain enzyme, the C-domain is the principal angiotensin-converting site and inhibition of the C-domain only with a C-domain-selective inhibitor leads to substantial suppression of Ang II formation even when the N-domain active site remains uninhibited. In contrast, both active sites hydrolyze the degradation of bradykinin and both active sites appear to be equally active in metabolizing BK in the the full-length, 2-domain enzyme. Thus, when either the N or the C domain is selectively inhibited by either an N-domain-specific or a C-domain-specific inhibitor, respectively, BK continues to be metabolized by the uninhibited active site. This fundamental discovery has resulted in the observation that treatment of a hypertensive animal (the high-renin mouse model) with the C-domain-specific ACE inhibitor Lis-Trp results in suppression of Ang II formation and reduction in blood pressure equivalent to that achieved with the conventional ACE inhibitor lisinopril (which, like all current-generation ACE inhibitors, is a mixed N- and C-domain inhibitor) while at the same time leaving BK levels unchanged; lisinopril, in contrast, produces substantial increases in plasma BK levels in this model, consistent with the known pharmacological profile of conventional ACE inhibitors [D. Burger et al. (2014) Effects of a domain-selective ACE inhibitor in a mouse model of chronic angiotensin II-dependent hypertension. *Clin. Sci.* 127: 57-63]. Increases in plasma BK levels are associated with episodes of ACE inhibitor- and vasopeptidase inhibitor-induced angioedema, cough, and other manifestations of excessive vasodilatation, leading to the unfavorable side effect and safety profile of these drugs. C-domain-specific ACE inhibitors, such as Lis-Trp, will have fundamentally improved side effect and safety profiles compared to conventional ACE inhibitors, as well as improved efficacy profiles in diseases in which excessive vasodilatation is undesirable and impairs the therapeutic effect.

Vasopeptidase inhibitors are mixed non-selective inhibitors of the N- and C-domain active sites of ACE plus the NEP active site. These compounds result in decreased Ang II levels, increased natriuretic peptide (ANP, BNP, and C-type NP) levels, increased bradykinin levels, and increased levels of a variety of other vasodilator peptides, including adrenomedullin. Vasopeptidase inhibitors are effective in lowering blood pressure in various forms of hypertension but efficacy in heart failure is only equivalent, but not superior, to conventional ACE inhibitors. Moreover, vasopeptidase inhibitors have a poor safety and side-effect profile compared to conventional ACE inhibitors, with a higher incidence and severity of angioedema, and a higher incidence of cough, flushing, facial redness, nausea, vomiting, diarrhea, and constipation.

It has now been found that the unfavorable safety and side-effect profile and the disappointing efficacy of vasopeptidase inhibitors in heart failure is due to excessive vasodilatation, which is primarily driven by very high levels of bradykinin that accumulate during pharmacologic therapy with these compounds. When both the N- and the C-domain active sites of ACE as well as the NEP active site are blocked simultaneously the normal metabolism of bradykinin is severely disturbed and there is an enormous and undesirable build-up of BK in the blood and in the tissues. This build-up in BK results in serious safety issues, including angioedema, cough, flushing, facial redness, nausea, vomiting, diarrhea, and constipation. Further, the enormous build-up of BK results in excess vasodilatation, which impairs pharmacological activity in heart failure, Vasodilator therapy is known to be effective in some forms of heart failure, especially acute heart failure. However, potent vasodilator therapy, e.g., with hydralazine-isosorbide dinitrate, results in excess mortality in chronic congestive heart failure when compared to therapy with the conventional ACE inhibitor enalapril [J. N. Cohn et al. (1991) A comparison of enalapril with hydralazine-isosorbide dinitrate in the treatment of chronic congestive heart failure. *N. Engl. J. Med.* 325: 303-10]. Treatment with the vasopeptidase inhibitor omapatrilat led to excessive vasodilatation, as evidenced by the increased incidence of angioedema, flushing, and facial redness, which limited the pharmacologic benefit in heart failure. Thus, on the one hand, omapatrilat results in a combined decrease in Ang II and increase in natriuretic peptides, producing a net beneficial effect expected to be greater than achieved by a conventional ACE inhibitor; on the other hand, however, omapatrilat results in high BK accumulation with excessive vasodilatation, which counteracts the aforementioned benefit. The net effect is that omapatrilat is no more effective in heart failure than a conventional ACE inhibitor in terms of therapeutic benefit and in fact is substantially worse in terms of the safety and side-effect profile.

It has now been found that the unfavorable safety and side-effect profile and the disappointing efficacy of vasopeptidase inhibitors is due to non-selective inhibition of the 2-domain ACE enzyme. All vasopeptidase inhibitors, including omapatrilat, inhibit both the N- and C-domain active sites of ACE; this together with simultaneous inhibition of NEP results in excessive build-up of vasodilator peptides, principally BK.

Since a C-dom/NEP inhibitor does not produce elevated BK levels, treatment of hypertension or heart failure does not result in unfavorable excessive vasodilatation and both the safety and efficacy profiles are optimized. Specifically, compared to placebo, there is no increased risk of angioedema, cough, flushing, facial redness, or gastrointestinal symptoms; further, compared to a conventional ACE inhibitor, a C-dom/NEP inhibitor shows superior efficacy in the treatment of hypertension and heart failure.

The invention will now be discussed in more detail, by way of example only, with reference to the following non-limiting examples.

EXAMPLE 1

Changes in Vasoactive Peptide Levels Induced by Combined ACE C-Domain/NEP Inhibition Ex Vivo in Human Plasma Synthesis of the ACE C-Domain-Selective Inhibitor Lis-Trp.

Lisinopril, which is one of the commercially available ACE inhibitors, is active with a nanomolar inhibition constant, and has been shown to be relatively safe in the treatment of patients with hypertension and acute myocardial infarction. It is therefore mostly used as the first-line treatment for hypertension and heart-related diseases. The phosphinic ACE inhibitor, RXP A380, is ~3,000-fold C-domain-selective and one key feature of the C-domain selectivity is the tryptophan moiety in the $P_2'$ position.

The synthesis of lisinopril incorporating a tryptophan moiety at the $P_2'$ position (Lis-Trp) was carried out as follows: The starting diastereomeric material 1 was prepared by the reductive amination of ethyl 2-oxo-4-phenyl butyrate and N-ε-(tert-butoxycarbonyl)-L-lysine using and ethanolic solution of $NaBH_3CN$. The ratio of the two diastereoisomers was observed as 55:45 from the $^1H$ NMR spectrum. Peptide coupling of the compound 1 with the L-tryptophan methyl ester 2 (prepared earlier by methylation of tryptophan in the presence of thionyl chloride and methanol according to the method described by Hvidt et al.) was effected using EDC.HCl in the presence of HOBt and diisopropyl ethyl amine as a base to afford the diastereomeric pseudopeptide 3 in 74% yield. The characterisation of this diastereomeric mixture 3 was achieved from the EI-MS and spectroscopic data, the EI-MS data indicated a molecular ion peak at 637 corresponding to $M^++H$. The $^1H$ NMR spectrum showed two singlets at δ 3.71 and 3.73 ppm corresponding to the two methoxy groups of the diastereomeric mixture 3. Acid hydrolysis of the resulting diastereomeric mixture 3 produces the hydrochloride salt of the diastereomeric mixture 4 in a quantitative yield. Evidence of the compound 4 was found from the disappearance of the Boc, methyl and ethyl signals on the $^1H$ NMR spectrum. Purification and separation of the diastereomeric mixture 4 was done by HPLC.

Initial attempts to remove the Boc group and concomitant hydrolysis of the ethyl and methyl esters under acid conditions at room temperature afforded a mixture of four products after HPLC separation and purification. These four products, $P_1$, $P_2$, $P_3$ and $P_4$, were as a result of incomplete hydrolysis of compound 3, since acid hydrolysis of esters at room temperature is relatively slow. The EI-MS data indicated molecular ion peaks at 522, 522, 536 and 536 for $P_1$, $P_2$, $P_3$ and $P_4$, respectively. However, the diastereomeric mixture 3 was stirred in 4N HCl at room temperature for 24 h, after which the solvent was evaporated and then the mixture stirred with a solution of 0.5N LiOH for a further 5 h to afford the desired product 4.

The characterisation of this diastereomeric mixture 4 was achieved from the EI-MS and spectroscopic data, and the EI-MS data indicated a molecular ion peak at 495 corresponding to $M^++H$. Purification and separation of the diastereomeric mixture 4 by HPLC gave the required two diastereoisomers in a 60:40 ratio.

Scheme 1

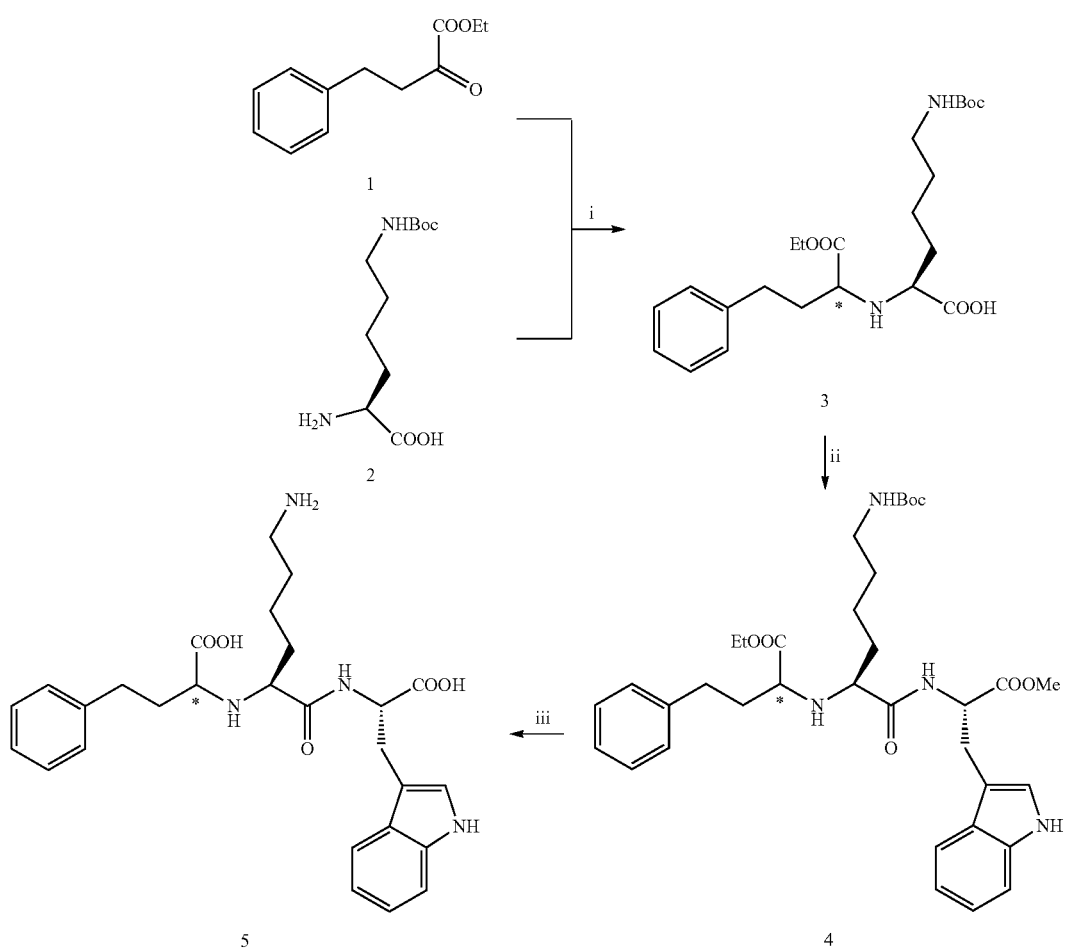

Reagents and conditions: (i) ketone 1 (4.0 eq), amino acid 2 (1.0 eq), NaBH$_3$CN (2.0 eq), 50% EtOH/H$_2$O, rt, 12 h; (ii) L-tryptophan methyl ester, EDC.HCl, HOBt, iPr$_2$NEt (1.0 equiv), dry DMF, rt, 72 h; (iii) (a) 4N HCl, EtOAc, rt, 24 h and (b) 0.5N LiOH, THF-MeOH, rt, 5 h.

Inhibition of ACE and NEP Activity and Determination of Angiotensin and Bradykinin Peptides in Human Plasma Ex Vivo.

Effects on Angiotensin Peptides. Equilibrium angiotensin peptide levels were measured in plasma samples after incubating Li-Heparin samples supplemented with recombinant human NEP (rhNEP) (R&D, 200 pg/ml) at controlled pH (7.4) for a period of 30 min at 37° C. in the presence and absence of indicated compounds and enzymes. Following equilibration, samples were stabilized and spiked with stable-isotope-labelled internal standards for each angiotensin metabolite, Ang I (Ang 1-10), Ang II (Ang 1-8), Ang 1-7, Ang 1-5, Ang 2-8, Ang 3-8, Ang 2-10, Ang 2-7, Ang 1-9, and Ang 3-7, at a concentration of 200 pg/ml. Following C18-based solid-phase-extraction, samples were subjected to LC-MS/MS analysis using a reversed-phase analytical column (Acquity UPLC® C18, Waters) operating in line with a XEVO TQ-S triple quadrupole mass spectrometer (Waters) in MRM mode. Angiotensin peptide concentrations were calculated by relating endogenous peptide signals to internal standard signals considering the corresponding response factors determined in appropriate calibration curves, provided that signals exceeded a signal-to-noise ratio of 10.

As shown in accompanying FIGS. 1A and B, it was found that combined treatment of human plasma with sacubitrilat (an NEP inhibitor) and Lis-Trp (an ACE C-domain-selective inhibitor) resulted in a 91.5% inhibition of equilibrium Ang 1-8 levels (Ang II), which was comparable with that of the inhibition observed in the presence of the unselective ACE/NEP inhibitor omapatrilat (93.1%) and less compared to the inhibition by the combination of sacubitrilat and lisinopril (>99%). In addition, treatment with sacubitrilat and Lis-Trp caused a significant increase in the cardioprotective heptapeptide Ang 1-7 compared to untreated or sacubitrilat-treated human plasma. In the presence of recombinant human ACE2, a carboxypeptidase that converts Ang 1-10 to Ang 1-9 and Ang II to Ang 1-7, expected changes in substrates and products of ACE2 were observed (decrease in Ang I and Ang II and increase in Ang 1-9 and Ang 1-7). A dramatic increase in Ang 1-9 was observed under combined inhibition of NEP and ACE when compared to treatment with solvent. Surprisingly, sacubitrilat/Lis-Trp led to a significant increase in levels of Ang 1-7 following treatment compared to sacubitrilat/lisinopril (39.0 vs. 28.1 pg/ml), while levels of cardioprotective Ang 1-7 remained undetectable in human plasma treated with omapatrilat. These data confirm that under ex vivo conditions in human plasma, treatment with sacubitrilat/Lis-Trp results in equivalent suppression of Ang II formation from Ang I as seen with omapatrilat and sacubitrilat/lisinopril, but with significantly higher accumulation of the cardioprotective peptide Ang 1-7 than observed with omapatrilat.

Effects on Bradykinin Peptides. The metabolism of a spike of bradykinin 1-9 (50 ng/ml) in 10% human plasma supplemented with 200 pg/ml rhNEP (R&D) in vitro, followed by LC-MS/MS-based quantification of the bradykinin metabolites bradykinin 1-9, 1-8, 1-7, 1-5, and 2-9 was examined. Briefly, samples where stabilized and spiked with 200 pg/ml of stable-isotope-labelled internal standards for bradykinin 1-9, 1-8, 1-7, 1-5, and 2-9. Following C18-based solid-phase-extraction, samples were subjected to LC-MS/MS analysis using a reversed-phase analytical column (Acquity UPLC® C18, Waters) operating in line with a XEVO TQ-S triple quadrupole mass spectrometer (Waters) in MRM mode. Bradykinin peptide concentrations were calculated by relating endogenous peptide signals to internal standard signals considering the corresponding response factors determined in appropriate calibration curves, provided that signals exceeded a signal-to-noise ratio of 10.

Figure 2A:
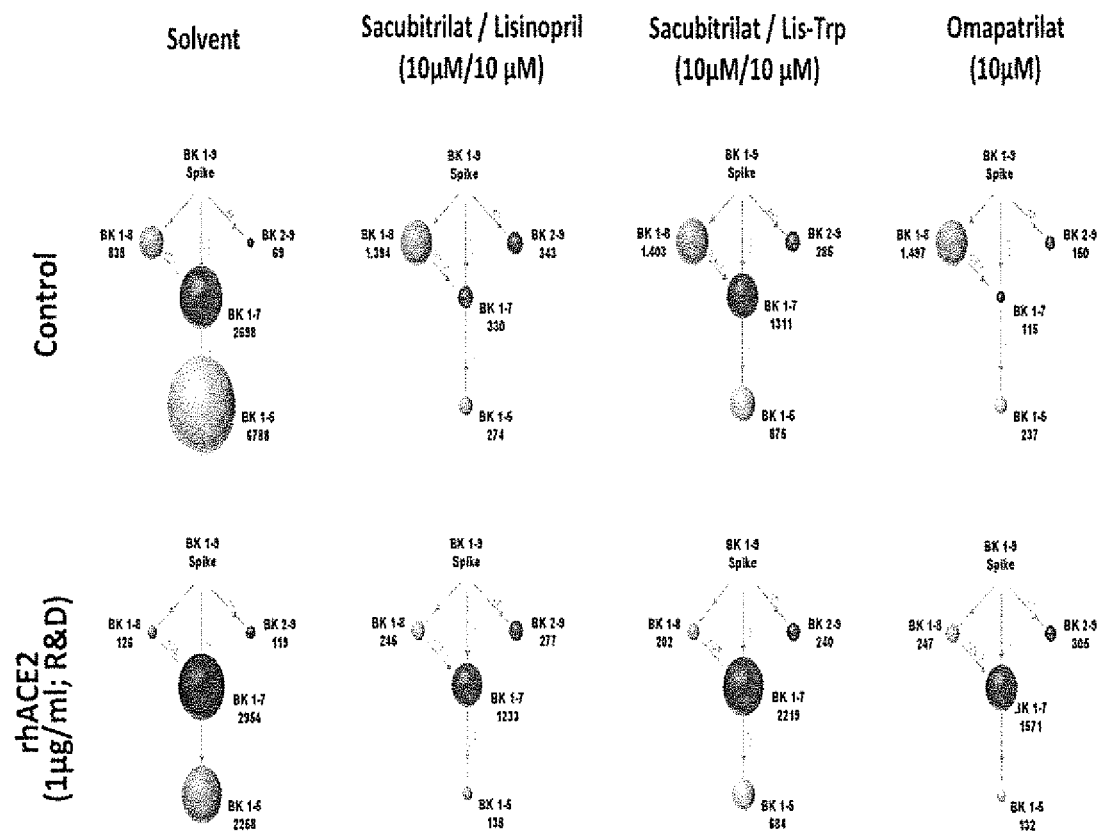
FIG. 2A represents the metabolism of bradykinin peptides in human plasma in the presence of 1% water (solvent), sacubitrilat and lisinopril, sacubitrilat and Lis-Trp, and omapatrilat. All samples were spiked with bradykinin 1-9 (BK1-9) at a concentration of 50 ng/ml followed by an incubation period at 37° C. Recombinant human neutral endopeptidase (rhNEP) was added to all samples at a concentration of 200 pg/ml. In the bottom panel recombinant human angiotensin-converting enzyme 2 (rhACE2) was added at a concentration of 1 µg/ml. The sizes of spheres reflect the concentration of the corresponding bradykinin metabolites. Concentrations for indicated metabolites are given in pg/ml.
Figure 2B:
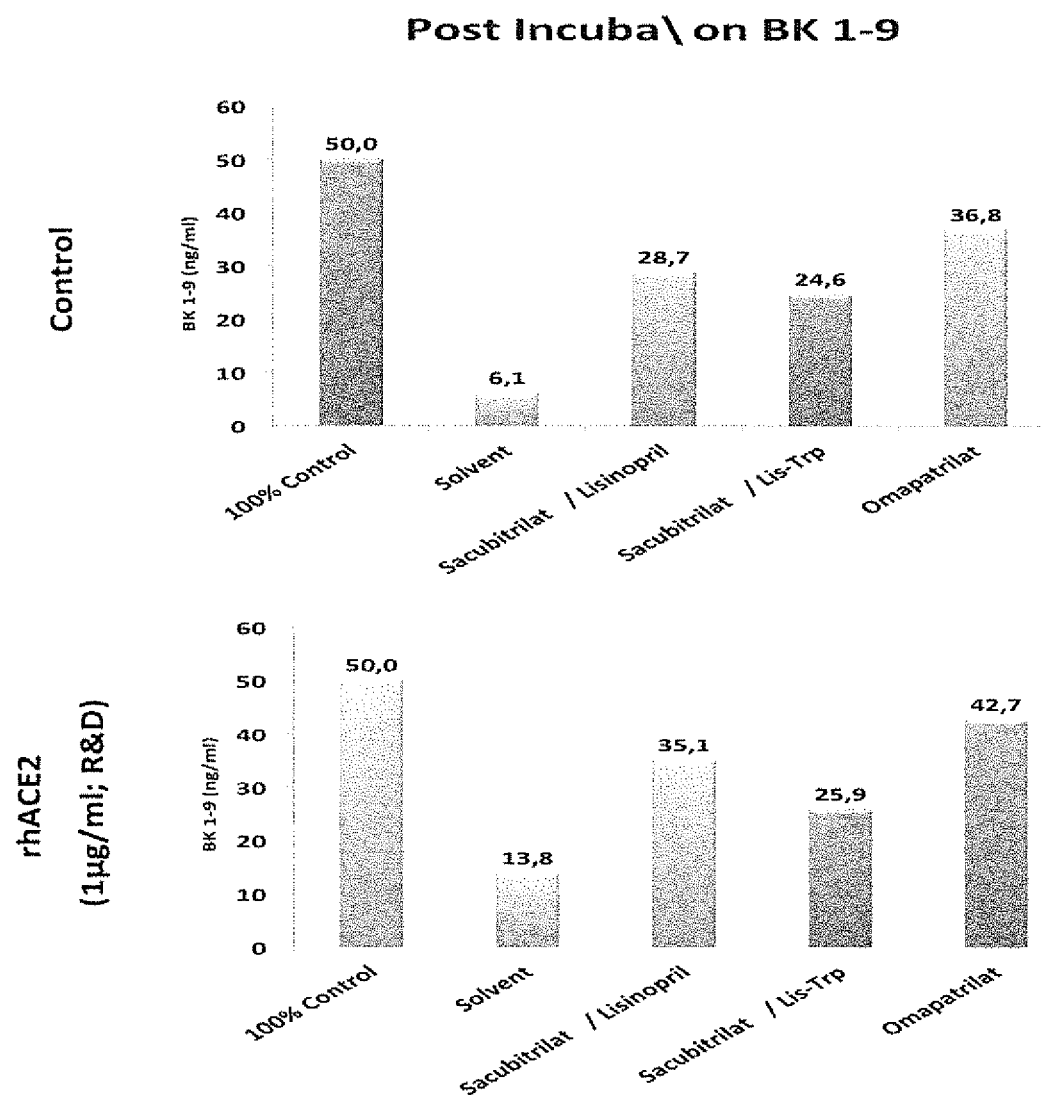
FIG. 2B is a graph that represents the concentrations of bradykinin in human plasma samples treated with reference to FIG. 2A and after incubation with water (solvent), sacubitrilat and lisinopril, sacubitrilat and Lis-Trp, and omapatrilat. The concentrations of BK 1-9 are relative to the control that was plasma spiked with BK 1-9 following the incubation period (100% spike control).

As shown in accompanying FIGS. 2A and B, it was found that treatment of human plasma with sacubitrilat/lisinopril, sacubitrilat/Lis-Trp and omapatrilat resulted in decreased metabolism of bradykinin due to the inhibition of ACE. However, in the case of sacubitrilat/Lis-Trp there was a significant increase in metabolism of bradykinin 1-9, as indicated by the levels of bradykinin 1-8, 1-7, and 1-5, compared to treatment with omapatrilat or sacubitrilat/lisinopril. Sacubitrilat/Lis-Trp resulted in a concomitant decrease in bradykinin 1-9. Compared to solvent control plasma, where up to 90% of the bradykinin 1-9 spike was converted to its downstream metabolites during the incubation period, NEP/ACE inhibitor combinations investigated resulted in drug-specific stabilization of the bradykinin 1-9 spike. While with omapatrilat 74-85% of the initial bradykinin 1-9 spike was recovered following the incubation period, only 49-52% of bradykinin 1-9 remained following incubation in the presence of sacubitrilat/Lis-Trp, confirming previous findings regarding downstream metabolites. Lisinopril's efficacy in bradykinin stabilization ranged between omapatrilat and sacubitrilat/Lis-Trp, with 57-70% of remaining bradykinin 1-9 spike. Addition of recombinant human ACE2 (1 µg/ml, R&D) to plasma led to decreased bradykinin 1-8 and increased bradykinin 1-7 and bradykinin 1-5 due to the hydrolysis of bradykinin 1-8 by ACE2. These data confirm that under ex vivo conditions in human plasma, treatment with sacubitrilat/Lis-Trp results in more efficient metabolism of bradykinin than omapatrilat or sacubitrilat-flisinopril, with significantly greater production of non-vasodilating bradykinin metabolites and reduced accumulation of bradykinin 1-9 compared to both omapatrilat and sacubitrilat/lisinopril.

Overall, these data confirm that a dual inhibitor compound that embodies selective inhibition of the ACE C-domain together with inhibition of NEP results in a unique and favourable peptide-metabolism profile, with efficient suppression of Ang II production, accumulation of the cardioprotective peptide Ang 1-7, and metabolism of bradykinin 1-9 to non-vasodilating downstream metabolites, bradykinin 1-7 and 1-5. This peptide-metabolism profile is distinct from the profile observed with a conventional vasopeptidase inhibitor such as omapatrilat and indicates unique pharmacological and therapeutic properties for dual C-dom/NEP inhibitor.

EXAMPLE 2

Efficacy of Combined ACE C-Domain/NEP Inhibition in the LinA3 Mouse Model of Hypertension LinA3 Mouse Model of Hypertension.

Circulating renin contributes by a pressure-independent mechanism to the production of angiotensin peptides in the heart of intact animals. To this end, a transgenic mouse model where human renin is over expressed has been developed [Prescott et al., (2000) Contribution of circulating renin to local synthesis of angiotensin peptides in the heart. *Physiol Genomics.* 4:67-73].

To express human renin in mouse liver, a 3-kb region of the transthyretin gene promoter was cloned upstream of the human prorenin cDNA. To generate active human renin, a cleavage site for the ubiquitous protease furin was inserted at the juncture of the prosegment and the active renin molecule, resulting in prosegment removal by endogenous proteases in the secretory pathway of expressing cells. Expression of human angiotensinogen in the mouse heart was achieved by cloning the cDNA downstream of a 6-kb fragment of the a-myosin heavy chain gene promoter. FVB/N mouse embryos were microinjected, and all subsequent breeding was carried out in the FVB/N line. Tissue-specific expression of the human transgenes was verified by an RNase protection assay from total tissue RNA.

These mice, termed TTRhRen, have slightly elevated plasma Ang II levels (1- to 2-times normal), are chronically hypertensive, and have frank cardiac hypertrophy by 10 to 12 weeks of age.

Experimental Procedure

Male C57BL6 mice (12-14 weeks) are assigned to 6 groups of 10 mice/group:
1. Vehicle
2. Lisinopril alone
3. Omapatrilat alone
4. Lis-Trp alone
5. Sacubitril alone
6. Sacubitril+Lis-Trp.

Blood Pressure

Blood pressure is measured by tail cuff (n=5/group) and telemetry (n=5/group). These techniques have previously been described in detail. Briefly, for tail cuff measurements, mice are habituated for the apparatus for one week prior to BP measurements. For telemetry, probes are surgically placed by an animal technician who has extensive experience in mouse surgical procedures.

Study Design

Lisinopril and the C-domain selective ACE inhibitor Lis-Trp are given at a dose of 10 mg/kg/day, based on published data [D. Burger et al. (2014) Effects of a domain-selective ACE inhibitor in a mouse model of chronic angiotensin II-dependent hypertension. *Clin. Sci.* 127: 57-63]. Lisinopril and the C-domain selective ACE inhibitor Lis-Trp are dissolved in saline and administered via osmotic minipumps for 4 weeks.

Justification of Animal Numbers

The decision to use 10 mice per group (5 each for tail cuff and telemetry measurement) is based on the inventors' experience of the heterogeneity of effects of Ang II on blood pressure elevation and antihypertensive responses in these mice. This number of mice provides about 80% power to detect a 10-15 mm Hg difference in systolic blood pressure between groups.

Summary of Protocol

Minipumps containing Ang II (600 ng/kg/min) are placed at week 1, after the radiotelemetry probes have been placed and once baseline blood pressure has been measured Blood pressure is measured by tail cuff (n=4/group) and by telemetry (n=4/group).

Blood is collected from the tail artery with the assistance, guidance and technical help of the ACVS staff.

Urine is collected by spot urine collections.

Heart, kidneys and aorta are collected at autopsy for molecular studies

Outcomes

C-domain selective ACE inhibitors such as Lis-Trp in combination with the NEP inhibitor sacubitril have a more profound blood pressure lowering effect than lisinopril alone and equivalent to omapatrilat, with associated decrease in bradykinin- and Ang II-mediated cardiac and renal remodelling and inflammation.

The invention claimed is:

1. A selective dual ACE/NEP inhibitor comprising Lis-Trp and sacubitrilat, wherein the dual ACE/NEP inhibitor is selective for the C-domain active site of ACE and for the NEP active site; and wherein Lis-Trp is modified Lisinopril comprising a tryptophan moiety in position $P_2'$ that confers angiotensin-converting enzyme selectivity for the C-domain active site sufficient to inhibit the conversion of angiotensin I to angiotensin II whilst preserving bradykinin metabolism.

2. The dual ACE/NEP inhibitor as claimed in claim 1, wherein the dual ACE/NEP inhibitor is provided in a pharmaceutical composition further comprising a pharmaceutically acceptable carrier, together with other optional pharmaceutically acceptable excipients.

3. The dual ACE/NEP inhibitor as claimed in claim 2, wherein the pharmaceutical composition is in the form of a tablet or capsule for oral administration.

4. The dual ACE/NEP inhibitor as claimed in claim 2, wherein the pharmaceutical composition is in a form for administration by a parenteral route.

5. A method of treating a cardiovascular disease, wherein the cardiovascular disease is selected from:
   a. hypertension (high blood pressure);
   b. heart failure, including congestive heart failure, heart failure with reduced left ventricular (LV) ejection fraction (HFrEF), heart failure with preserved LV ejection fraction (HFpEF), left ventricular dysfunction, right-sided heart failure, right ventricular dysfunction, and general states of reduced cardiac output;
   c. atherosclerosis and atherosclerotic vascular disease, including coronary heart disease and coronary artery disease;
   d. myocardial infarction (heart attack), including acute coronary syndrome;
   e. nephropathy (kidney dysfunction) associated with hypertension or diabetes;
   f. stroke, including infarction of the brain or any part of the brain due to cerebral artery occlusion, thrombosis, or haemorrhage,
      comprising administering to a patient in need of such treatment a therapeutically effective amount of a selective dual ACE/NEP inhibitor comprising Lis-Trp and sacubitrilat, the dual ACE/NEP inhibitor being selective for the C-domain active site of ACE and for the NEP active site; and wherein Lis-Trp is modified Lisinopril comprising a tryptophan moiety in position $P_2'$ that confers angiotensin-converting enzyme selectivity for the C-domain active site sufficient to inhibit the conversion of angiotensin I to angiotensin II whilst preserving bradykinin metabolism.

6. The method of claim 5, wherein the dual ACE C-domain/NEP inhibitor is administered by an oral route in the form of a tablet, capsule, or other pharmaceutical formulation suitable for oral administration.

7. The method of claim 6, wherein the oral administration is once per day, twice per day, three times per day, or four times per day.

8. The method of claim 5, wherein the dual ACE C-domain/NEP inhibitor is administered by a parenteral route in a pharmaceutical formulation suitable for parenteral administration.

9. The method of claim 8, wherein parenteral administration is intravenously, intramuscularly, or subcutaneously.

10. The method of claim 8, wherein the parenteral administration is once per day, twice per day, three times per day, or four times per day.

11. A composition comprising a combination of Lis-Trp, an inhibitor selective for the C-domain active site of ACE and sacubitrilat, an inhibitor of the NEP active site, Lis-Trp being modified Lisinopril comprising a tryptophan moiety in position $P_2'$ that confers angiotensin-converting enzyme selectivity for the C-domain active site sufficient to inhibit the conversion of angiotensin I to angiotensin II and the breakdown of natriuretic peptides whilst preserving bradykinin metabolism.

12. A method for treatment of a cardiovascular disease comprising administering a composition according to claim 11, where such cardiovascular disease is selected from:
   a. hypertension (high blood pressure);
   b. heart failure, including congestive heart failure, heart failure with reduced left ventricular (LV) ejection fraction (HFrEF), heart failure with preserved LV ejection fraction (HFpEF), left ventricular dysfunction, right-sided heart failure, right ventricular dysfunction, and general states of reduced cardiac output;
   c. atherosclerosis and atherosclerotic vascular disease, including coronary heart disease and coronary artery disease;
   d. myocardial infarction (heart attack), including acute coronary syndrome;
   e. nephropathy (kidney dysfunction) associated with hypertension or diabetes;
   f. stroke, including infarction of the brain or any part of the brain due to cerebral artery occlusion, thrombosis, or hemorrhage.

13. The method of claim 12, wherein the composition is administered by an oral route in a form that combines both compounds (the ACE C-domain inhibitor and the NEP inhibitor) in a single formulation, where such formulation is a tablet, capsule, or other pharmaceutical formulation suitable for oral administration.

14. The method of claim 13, wherein the oral administration is once per day, twice per day, three times per day, or four times per day.

15. The method of claim 12, wherein the combination is administered by a parenteral route, in a pharmaceutical formulation that combines both compounds (the ACE C-domain inhibitor and the NEP inhibitor) in a single formulation suitable for parenteral administration.

16. The method of claim 15, wherein the parenteral administration is intravenously, intramuscularly, or subcutaneously.

17. The method of claim 15, wherein the parenteral administration is once per day, twice per day, three times per day, or four times per day.

\* \* \* \* \*